United States Patent [19]
Iijima et al.

[11] Patent Number: 5,614,966
[45] Date of Patent: Mar. 25, 1997

[54] OPHTHALMOLOGIC INSTRUMENT

[75] Inventors: Hiroshi Iijima; Mineki Hayafuji, both of Tokyo, Japan

[73] Assignee: Kabushiki Kaisha Topcon, Tokyo, Japan

[21] Appl. No.: 548,866

[22] Filed: Oct. 26, 1995

[30] Foreign Application Priority Data

Oct. 26, 1994 [JP] Japan .................................. 6-262608
Jan. 25, 1995 [JP] Japan .................................. 7-009968

[51] Int. Cl.$^6$ .................................................. A61B 3/14
[52] U.S. Cl. .................................................. 351/208
[58] Field of Search .................................. 351/205, 207, 351/208, 211, 221

[56] References Cited

U.S. PATENT DOCUMENTS

5,465,123  11/1995  Iijima ........................ 351/208

Primary Examiner—Huy Mai
Attorney, Agent, or Firm—Foley & Lardner

[57] ABSTRACT

In order to detect an alignment state while watching an index image, illumination light is first projected onto an anterior segment of a subject's eye (E) from LEDs (21), and then light emitted by another LED (31) is guided to a cornea (C) through an alignment light projecting optical system (30). The light emitted by the LEDs (21, 31) and reflected by the subject's eye (E) is imaged on a CCD camera (26) through an image-formation optical system (20). An index image (SP) and an anterior segment image (E') which are of the reflection light guided to the CCD camera (26) are displayed on a screen (28). The index image (SP) is received by a sensor (46). Based on information about received light obtained by the sensor (46), a comparator (47) detects information about alignment of the subject's eye (E) with an instrument body. According to a detection result obtained by the comparator (47), a display state of the display (28) is changed, so that an operator judges that a desired state of alignment is nearing.

3 Claims, 7 Drawing Sheets

OPHTHALMOLOGIC INSTRUMENT

BACKGROUND OF THE INVENTION

1. Field of the Invention

This invention relates to an ophthalmologic instrument capable of displaying an alignment state when alignment of a subject's eye with an instrument body is adjusted to observe the subject's eye.

2. Description of the Prior Art

An ophthalmologic instrument is known in which an image of an anterior segment of a subject's eye is displayed at the middle of a display screen of a means for observing the eye and, in addition, an alignment level mark is displayed at the corner of the display screen simultaneously with the image of the anterior segment. The alignment level mark gradually changes in real time in accordance with the state of alignment, and thereby an operator can judge whether the alignment has been precisely adjusted or not.

There is also an ophthalmologic instrument, such as a non-contact type of tonometer, in which great accuracy in alignment is required. In this ophthalmologic instrument, rough alignment of the subject's eye with the instrument is first carried out by estimating it directly with the operator's eye or by observing an image of the subject's eye displayed on a display screen, and then fine alignment is carried out by checking an alignment level mark displayed on the display screen.

However, since the alignment level mark merely serves to inform the operator of an alignment state step by step, the operator disadvantageously cannot determine a direction in which the instrument body is moved with respect to the subject's eye in order to complete the alignment.

As a solution to this problem, an idea has been proposed that an index image is used to adjust alignment of the instrument body with the subject's eye in up, down, right, and left directions whereas an alignment level mark is used to determine a working distance between the instrument body and the subject's eye. The index image is a corneal reflection image formed by projecting a beam of index light for alignment onto a cornea of the subject's eye. The operator moves the instrument body in the up, down, right, and left directions so as to bring about a coincidence between a predetermined position on the display screen and a position of the index image superimposed on an image of the anterior segment of the subject's eye.

In this connection, there is a need to individually ascertain the index image and the alignment level mark for the alignment if they are individually displayed. In addition, in such an ophthalmologic instrument requiring the pinpoint accuracy as mentioned above, it is difficult to determine the working distance by the alignment level mark displayed at the corner of the display screen because the operator must carry out the alignment while watching the index image which is displayed in the middle of the display screen and is continuously trembling under the influence of the involuntary eye movement of the subject's eye.

SUMMARY OF THE INVENTION

It is therefore an object of the present invention to provide an ophthalmologic instrument in which a working distance between a subject's eye and the instrument can be ascertained while watching an index image for alignment and therefore overall alignment can be easily carried out.

In order to achieve the object, the ophthalmologic instrument according to the present invention comprises an anterior segment illuminating light source for illuminating an anterior segment of a subject's eye, an alignment light projecting optical system for guiding a beam of light emitted by an alignment light source to a cornea of the subject's eye, an image forming optical system for forming an image of the anterior segment and an image of the cornea on an image forming surface which are formed such that beams of light emitted by the light sources are reflected by the subject's eye, and a display means for displaying the images of the anterior segment and the cornea formed on the image forming surface. The ophthalmologic instrument further comprises an alignment detecting optical system for guiding the image of the cornea to a light receiving means different from the image forming surface, and an alignment detecting means for detecting alignment of the subject's eye with an instrument body from information about received light obtained by the light receiving means. In the ophthalmologic instrument, a judgment that alignment is approaching a desired state is formed by changing a display state on the display means in accordance with a detection result obtained by the alignment detecting means.

DETAILED DESCRIPTION OF THE PREFERRED EMBODIMENTS

Embodiments of an ophthalmologic instrument according to the present invention will be described with reference to the attached drawings.

(First Embodiment)

Figure 1:
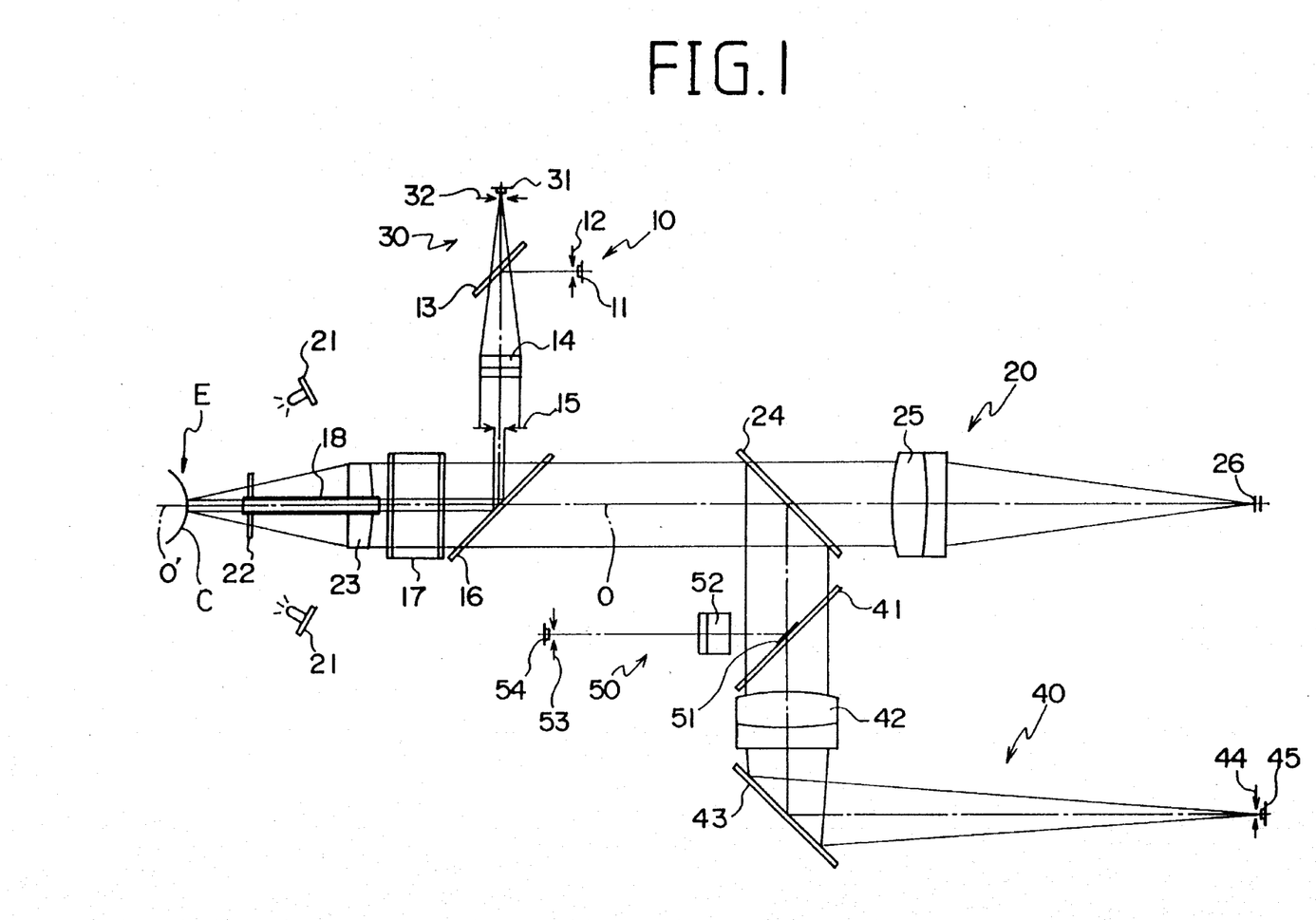
FIG. 1 is a schematic view of optical systems of the ophthalmologic instrument according to the present invention, showing a state in which a subject's eye is observed.

In FIG. 1, reference numeral 10 designates an optical system for projecting a target, on which a subject's eye is fixed, onto the subject's eye.

The target projecting optical system 10 includes an LED 11, an aperture stop 12, a wavelength dividing filter 13, a collimeter lens 14, a diaphragm 15, a half mirror 16, a chamber window 17, and an injection nozzle 18.

The LED 11 emits visible light which becomes a target image. The wavelength dividing filter 13 serves to reflect visible light and transmit near infrared light. The chamber window 17 is frame-shaped to surround a supplier, such as a cylinder member, which supplies the injection nozzle 18 with pulsed air.

The visible light emitted from the LED 11 passes through the aperture stop 12 and is reflected by the wavelength dividing filter 13. The visible light reflected by the wavelength dividing filter 13 is made parallel rays of light by the collimator lens 14. The parallel rays of light is then made a diaphragm image by the diaphragm 15. The diaphragm image is reflected by the half mirror 16 and then passes through the chamber window 17. The diaphragm image which has passed through the chamber window 17 reaches a cornea C of the subject's eye E through the injection nozzle 18. The subject's eye is fixed on the diaphragm image formed on the cornea C. Visible light reflected by the cornea C is reflected by an objective lens 23 so as not to enter the other elements disposed after the objective lens 23.

Reference numeral 20 designates an image-formation optical system. The image-formation optical system 20 can be used both as an optical system for detecting alignment of an optical axis O with a visual axis O' of the subject's eye E in up, down, right, and left directions and as an optical system for observing an image of the subject's eye E and the anterior segment.

The image-formation optical system 20 includes a plurality of LEDs 21, a cover glass 22, the objective lens 23, the chamber window 17, the half mirror 16, a half mirror 24, an image-formation lens 25, and a CCD camera 26.

The LEDs 21 emit infrared light. The LEDs 21 also directly illuminate the subject's eye E from right and left in order to observe the anterior segment of the eye E. The cover glass 22 is fastened to the tip of the injection nozzle 18. The objective lens 23 reflects visible light.

The infrared light emitted from the LEDs 21 is reflected by the subject's eye E and then passes through the cover glass 22. The infrared light which has passed through the cover glass 22 is made parallel rays of infrared light by the objective lens 23. The parallel rays of infrared light pass through the chamber window 17, the half mirror 18, and the half mirror 24 and then are condensed by the image-formation lens 25. The condensed infrared light becomes an image on the CCD camera 26.

Figure 2A:
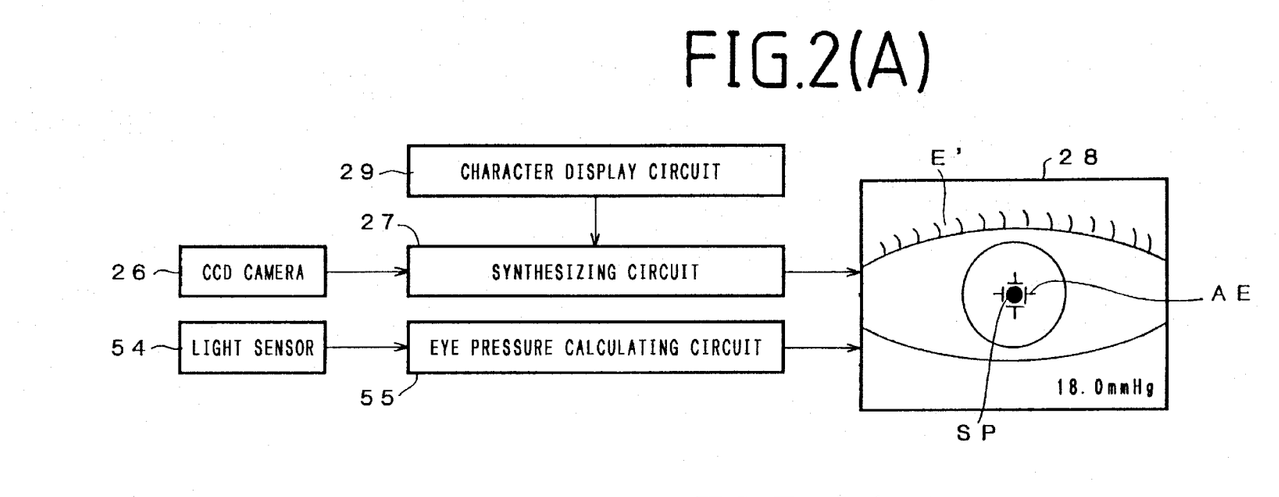
FIG. 2(A) is a block diagram of component parts which function to display an image.

As shown in FIG. 2(A), the infrared reflection light imaged on the CCD camera 26 is input to a synthesizing unit 27 by which the infrared reflection light is transformed into a signal. The signal is then displayed on the display screen 28 in the form of an image E' of the anterior segment of the subject's eye E. On the display screen 28, an alignment area AE is superimposed on the image E' in accordance with a character signal output by a character displaying unit 29.

Reference numeral 30 designates an optical system for projecting alignment detection light onto the subject's eye E. The alignment detection light projecting optical system 30 includes an LED 31, an aperture stop 32, the wavelength dividing filter 13, the collimator lens 14, the diaphragm 15, the half mirror 16, the chamber window 17, and the injection nozzle 18. The LED 31 as an alignment light source emits near infrared light. The optical system 30 including the LED 31 can be also used as an optical system for projecting flatness detection light onto the subject's eye E when eye pressure is measured, which will be described later.

The near infrared light omitted by the LED 31 passes through the aperture stop 32 and the wavelength dividing filter 13. The near infrared light is then made parallel rays of near infrared light by the collimator lens 14. The parallel rays become a diaphragm image by the diaphragm 15, and then the diaphragm image is reflected by the half mirror 16. Thereafter, the diaphragm image reaches the cornea C of the subject's eye E through the chamber window 17 and the injection nozzle 18, and then is reflected by the cornea C.

The light reflected by the cornea C passes through the cover glass 22 of the image-formation optical system 20 and then is made parallel rays of reflection light by the objective lens 23. The parallel rays pass through the chamber window 17, the half mirror 16, and the half mirror 24, and then are condensed by the image-formation lens 25. The condensed light is imaged on the CCD camera 26 in the form of an index image SP.

Reference numeral 40 designates an alignment optical system for detecting a working distance between the instrument and the subject's eye E. The alignment optical system 40 includes the cover glass 22, the objective lens 23, the chamber window 17, the half mirror 16, the half mirror 24, a center mirror 41, an image-formation lens 42, a total reflection mirror 43, a diaphragm 44, and a received-light detecting sensor 45.

The light emitted by the LED 31 and reflected by the cornea C passes through the cover glass 22 and then is made parallel rays of light by the objective lens 23. The parallel rays of light pass through the chamber window 17 and the half mirror 16, and then are reflected by the half mirror 24. The parallel rays of light reflected by the half mirror 24 pass through the peripheral part of the center mirror 41, and then are condensed by the image-formation lens 42. The condensed light is reflected by the total reflection mirror 43 and then passes through the diaphragm 44, and is imaged on the sensor 45.

Figure 2B:
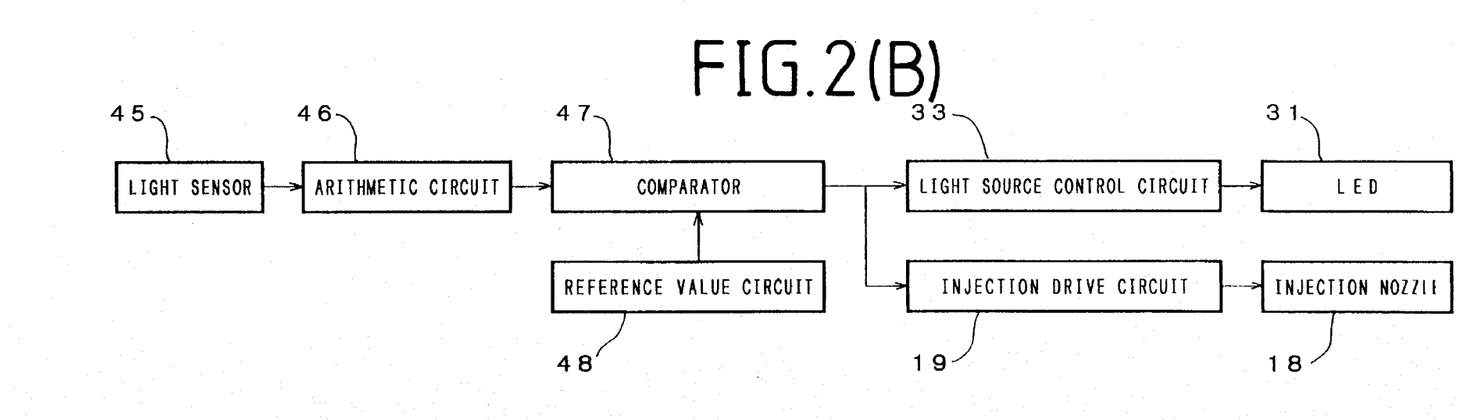
FIG. 2(B) is a block diagram of component parts which function as a drive mechanism.

As shown in FIG. 2(B), a quantity level of the light imaged on the sensor 45 is calculated by an arithmetic circuit 46. The calculated quantity level is output to a comparator 47 in the form of a level signal. A reference value circuit 48 outputs either of two level signals, which respectively correspond to two quantity levels of light, to the comparator 47 serving as an alignment detecting means.

One of the two level signals corresponds to a quantity level of light less than that of light received by the sensor 45 when alignment is completed. The other level signal corresponds to a quantity level of light equal to that of light received by the sensor 45 when alignment is completed. Accordingly, based on a quantity level of light received by the sensor 45, the comparator 47 can judge whether the completion of alignment is nearing or alignment has been completed.

For instance, if a level signal output by the arithmetic circuit 46 exceeds the lower quantity level of light, the comparator 47 outputs a switch signal to a light source control circuit 33, and thereby the light source control circuit 33 changes the LED 31 from a lighting state to a flickering state. If the level signal output by the arithmetic circuit 46 becomes equal to the higher quantity level of light, the comparator 47 outputs a switch signal to the light source control circuit 33, and thereby the light source control circuit 33 changes the LED 31 from the flickering state to the lighting state to become the original state, and simultaneously with the output of the switch signal, the comparator 47 outputs an injection signal to an injection drive circuit 19. According to the injection signal, the injection drive circuit 19 causes the injection nozzle 18 to jet pulsed air.

Reference numeral 50 designates an optical system for optically detecting the deformation of the cornea C. The corneal deformation detecting optical system 50 includes the cover glass 22, the objective lens 23, the chamber window 17, the half mirror 16, the half mirror 24, a total reflection mirror 51 disposed in the middle of the center mirror 41, an image-formation lens 52, a diaphragm 53, and a received-light detecting sensor 54.

The cornea C is made flat by pulsed air jetted from the injection nozzle 18. At the same time, detection light projected from the LED 31 onto the cornea C is reflected by the cornea C. The reflection light from the flattened cornea C passes through the cover glass 22 and then is made parallel rays of light by the objective lens 23. The parallel rays of light pass through the chamber window 17 and the half mirror 16, and then are reflected by the half mirror 24 and the total reflection mirror 51. The parallel rays of light are then condensed by the image-formation lens 52. The condensed light passes through the diaphragm 53 and then is imaged on the sensor 54.

As the cornea C becomes flatter, a quantity of light received by the sensor 54 increases. For this reason, as shown in FIG. 2(A), the sensor 54 outputs an increase signal generated according to the deformation of the cornea C to an eye pressure calculating circuit 55, and thereby the eye pressure calculating circuit 55 calculates an eye pressure of the subject's eye under a known procedure. A measurement result is displayed on the display screen 28.

A description will now be given of consecutive action ranging from the alignment to the measurement carried out through the optical systems described above.

First, the LED 11 is turned on so that the subject's eye can be fixed on a target which is visible light presented on the cornea C of the subject's eye E through the target projecting optical system 10. On the other hand, infrared light emitted by the LED 31 is projected onto the cornea C through the alignment detection light projecting optical system 30, and then is reflected by the cornea C. The operator (oculist) observes an image E' of the anterior segment of the eye E together with an alignment area image AE displayed on the display screen 28. The image E' of the anterior segment is formed such that infrared light directly projected onto the subject's eye E from the LED 21 is reflected by the eye E and then is imaged on the CCD camera 26.

Light emitted by the LED 31 and reflected by the cornea C is imaged on the CCD camera 26 through the image-formation optical system 20 and, at the same time, is received by the sensor 45 through the alignment optical system 40.

The operator operates the instrument so that, based on the reflection light imaged on the CCD camera 26 through the image-formation optical system 20, an index image SP appearing on the display screen 28 is placed within the alignment area AE.

While the index image SP is approaching the alignment area AE, a quantity of light imaged on the sensor 45 increases in response to the movement of the index image SP. The quantity level of light on the sensor 45 is compared with the level signal of the lower quantity level by means of the comparator 47. Based on the comparison result, the comparator 47 outputs a switch signal to the light source control circuit 33 in order to change the LED 31 from the lighting state to the flickering state.

The operator watches the index image SP flickering on the display screen 28, which shows that the alignment is almost completed, and again continues adjusting the alignment. At this time, a quantity of light of the LED 21 for observing the anterior segment of the eye E may be lessened to make the displayed index image SP clear.

When the comparator 47 detects the coincidence between the level signal of the higher quantity level and the maximum quantity level of light received by the sensor 45, the comparator 47 returns the flickering state of the LED 31 to the lighting state. At the same time, the comparator 47 instructs the injection drive circuit 19 to jet pulsed air from the injection nozzle 18. The pulsed air flattens a circular section of the cornea C. The detection light emitted from the LED 31 to the cornea C is reflected by the flattened cornea C and then is imaged on the sensor 54 through the corneal deformation detecting optical system 50.

The sensor 54 outputs an increase signal of a quantity level of received light, which increases as the cornea C becomes flatter, to the eye pressure calculating circuit 55, and thereby the eye pressure calculating circuit 55 calculates an eye pressure of the subject's eye under the known procedure. A measurement result is displayed on the display screen 28.

Second Embodiment

Figure 3:
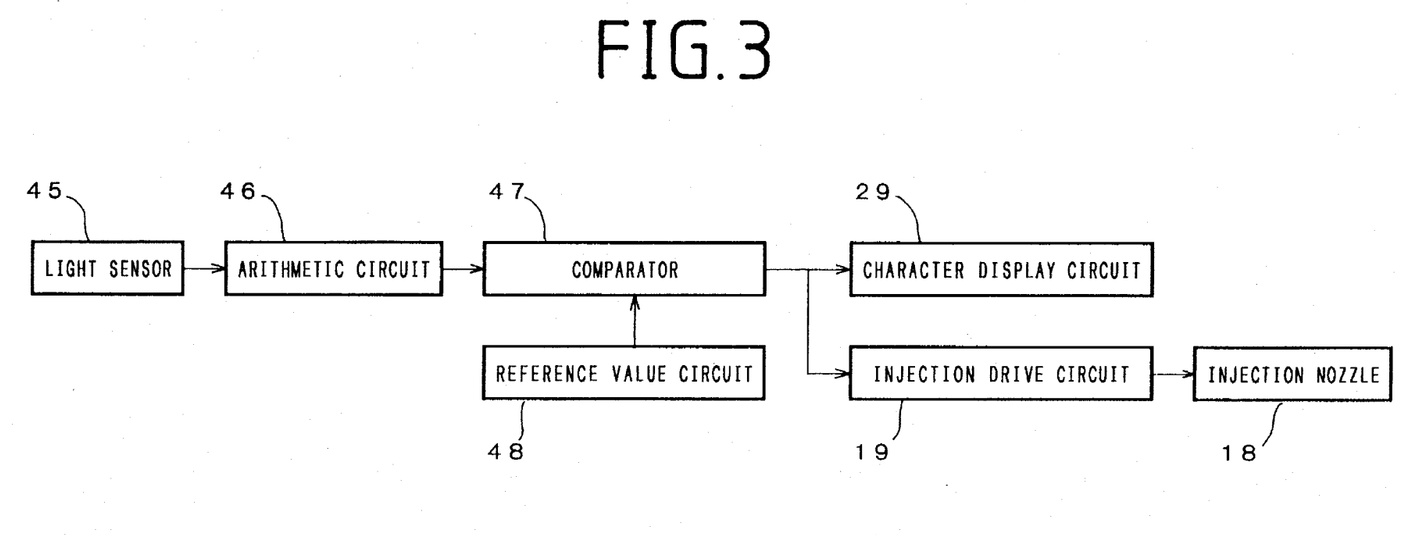
FIG. 3 is a block diagram of component parts which function as a drive mechanism, showing a second embodiment of the present invention.

In the first embodiment, in order to show the operator that alignment is almost completed, a switchover between a lighting state and a flickering state is performed for the index image SP displayed on the display screen 28. FIG. 3 shows an alternative to the above method.

Based on a comparison result of a quantity level of light received by the sensor 45, the comparator 47 outputs a switch signal to the character displaying unit 28. By the switch signal, a display state of the alignment area AE is changed from a lighting state to a flickering state or from a display color to another display color on the screen 28. From the switchover of the display state of the alignment area AE, the operator can judge that the completion of alignment is nearing.

At that time, the index image SP is placed in the vicinity of the alignment area AE. Accordingly, since the alignment area AE also comes within the field of vision of the operator, an operator's stare to the index image SP during alignment does not hinder the alignment.

Third Embodiment

FIGS. 4 to 7 show a third embodiment of the present invention. In this embodiment, the switchover between a lighting state and a flickering state of the index image SP is performed in an opposite manner to that in the first embodiment.

Figure 4:
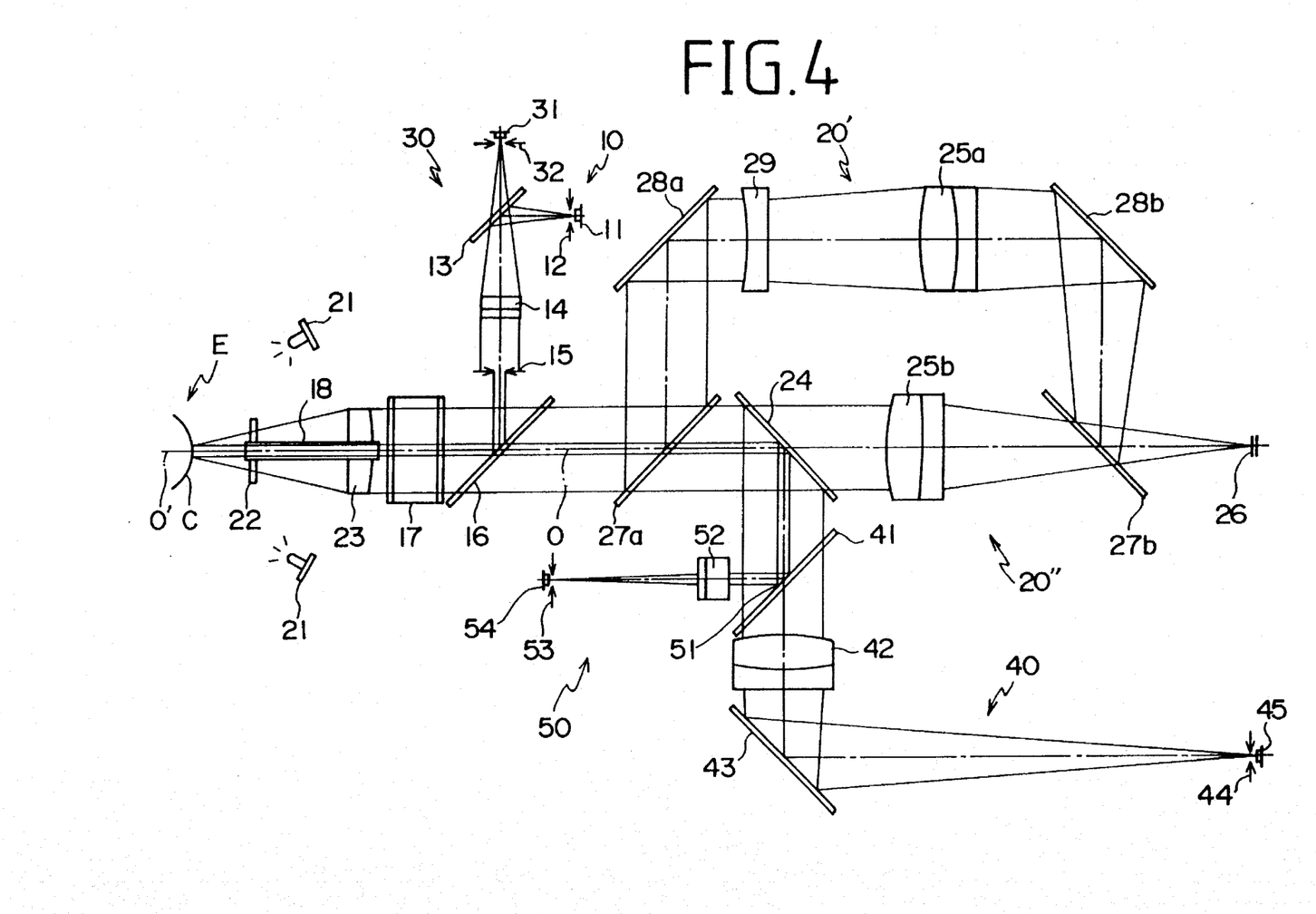
FIG. 4 is a schematic view of optical systems of the ophthalmologic instrument, showing a third embodiment of the present invention.

In FIG. 4, reference numeral 10 designates a target projecting optical system, reference numeral 20' designates an anterior segment observing optical system as an image-formation optical system for observing an image of the subject's eye E and the anterior segment thereof, reference numeral 20" designates an alignment detecting optical system for detecting alignment of an optical axis O with a visual axis O' of the subject's eye E, reference numeral 30 designates an alignment detection light projecting optical system, reference numeral 40 designates an alignment detecting optical system, and reference numeral 50 designates a corneal deformation detecting optical system.

In FIG. 4, the same numerals and characters are given to the same component parts as those of the first embodiment, and a description thereof is omitted. In addition, the respective dispositions of the target projecting optical system 10 and the alignment detection light projecting optical system 30 may be replaced with each other. If so, the wavelength dividing filter 13 shows opposite wavelength reflection and opposite transmission characteristics. The anterior segment observing optical system 20' includes a plurality of LEDs 21, a cover glass 22, an objective lens 23, a chamber window 17, and a half mirror 16 as the image-formation optical system 20 does, and moreover includes a half mirror 27a, a total reflection mirror 28a, a movable lens 29, and image-formation lens 25a, a total reflection mirror 28b, a half mirror 27b, and a CCD camera 26.

Infrared light emitted by the LED 21 is reflected by the subject's eye E. The infrared light reflected thereby passes through the cover glass 22 and then is made parallel rays of infrared light by the objective lens 23. The parallel rays of infrared light pass through the chamber window 17 and the half mirror 16, and then are reflected by the half mirror 27a and the total reflection mirror 28a. The parallel rays of infrared light then pass through the movable lens 29 and the image-formation lens 25a by which the parallel rays are condensed. Thereafter, the parallel rays of infrared light are reflected by the total reflection mirror 28b and the half mirror 27b, and then are imaged on the CCD camera 26.

The alignment detecting optical system 20'' includes the cover glass 22, the objective lens 23 which reflects visible light, the chamber window 17, the half mirror 16, the half mirror 27a, a half mirror 24, an image-information lens 25b, the half mirror 27b, and the CCD camera 26.

Light emitted by the LED 31 is reflected by the cornea C and then passes through the cover glass 22. The reflection light which has passed through the cover glass 22 is made parallel rays of light by the objective lens 23. The parallel rays of light pass through the chamber window 17, the half mirror 16, the half mirror 27a, and the half mirror 24, and then are condensed by the image-formation lens 25b. The condensed light passes through the half mirror 27b and then is imaged on the CCD camera 26 in the form of an index image SP.

Figure 5:
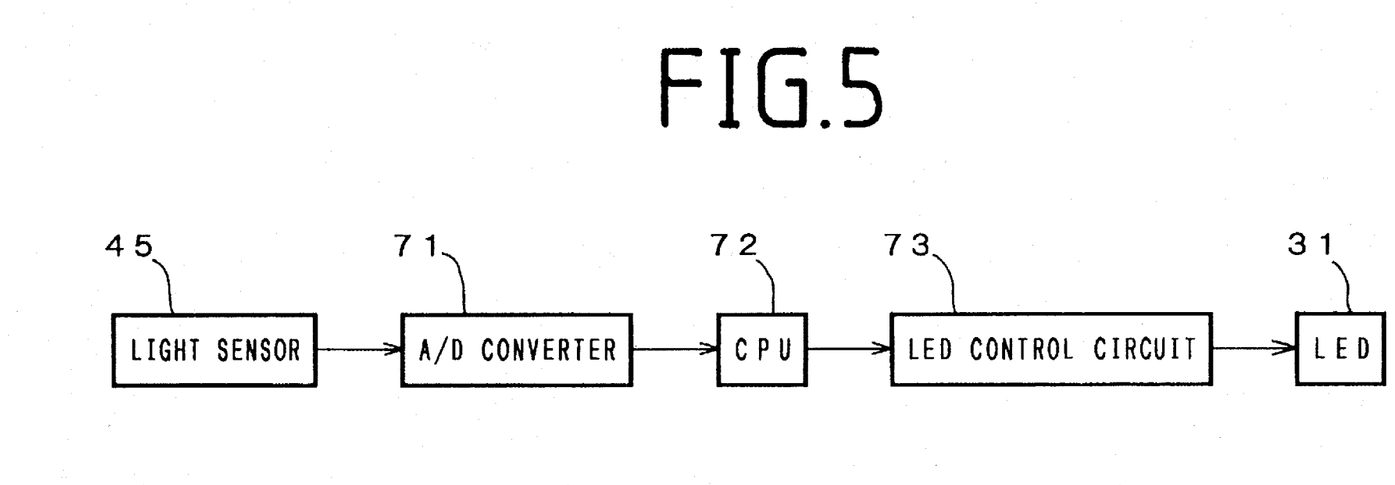
FIG. 5 is a block diagram of component parts relative to an alignment light source.

At this time, as shown in FIG. 5, the sensor 45 receives the alignment detection light emitted by the LED 31 and outputs information about a state of received light (about alignment detection state) to a CPU 72 via an A/D converter 71. Based on the state of the received light, the CPU instructs an LED control circuit 73 to change an emission state of the LED 31 from a lighting state to a flickering state and vice versa.

In more detail, if the CPU 72 judges that alignment of the subject's eye with the instrument body is quite unsatisfactory, the CPU 72 instructs the LED control circuit 73 to turn on and off the LED 31 alternately. Accordingly, the operator can observe an image of the anterior segment displayed on the display screen 28 (see FIG. 2) more clearly and can locate the index image SP more easily than the situation in which the LED 31 is always lighting as in the first embodiment. On the other hand, if the CPU 72 judges that the alignment is almost completed, the CPU 72 instructs the LED control circuit 73 to change the LED 31 from the blinking state to the lighting state. As a result, since the operator can easily observe the index image SP, the alignment can be easily carried out.

Figure 6A:
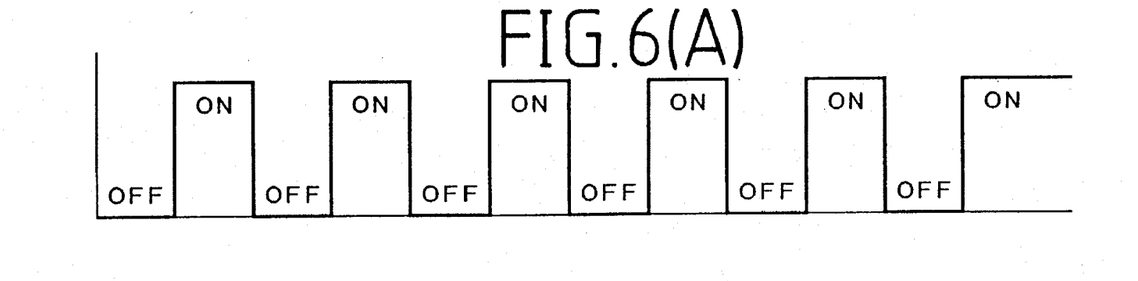
FIG. 6(A) is a timing chart of ON and OFF states of the alignment light source brought about when alignment is carried out.

For instance, as shown in FIG. 6(A), at the beginning of alignment, the LED 31 is turned on and off alternately, so that the index image SP displayed on the screen 28 flickers.

Figure 6B:
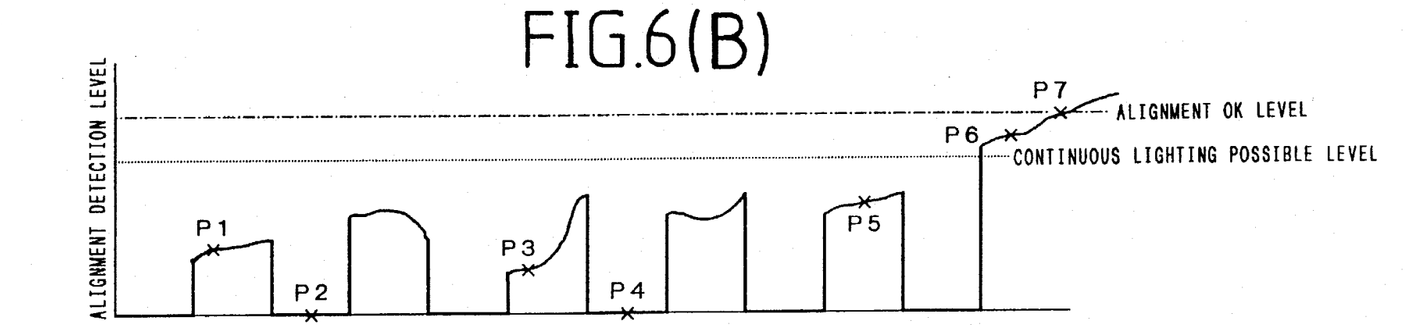
FIG. 6(B) is a chart of quantity levels of light detected by a sensor in accordance with the ON and OFF states of the alignment light source.
Figure 6C:
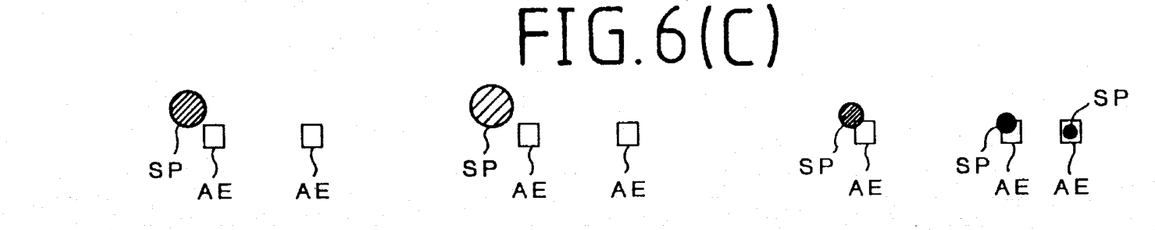
FIG. 6(C) shows a relationship between an alignment level mark and a reflection image of a cornea of the subject's eye.

At this time, since the sensor 45 also receives the alignment reflection light only when the LED 31 is turned on, the CPU 72 detects a quantity level of the received light, as shown in FIG. 6(B). As shown in FIG. 6(C), when the LED 31 is turned on, both of the alignment area mark AE and the index image SP are displayed whereas, when the LED 31 is turned off, only the alignment area mark AE is displayed.

When the completion of alignment is nearing and thereby the quantity level of light received by the sensor 45 exceeds a predetermined level, the LED 31 is changed from the blinking state to the lighting state. At this time, watching the lighting index image SP, the operator conducts a swift operation for alignment so as to position the index image SP within the alignment area mark AE. When the alignment is completed, the measurement of the subject's eye is started.

In the consecutive operation for alignment, in order to vary the size or density of the index image SP in accordance with a quantity level of light received by the sensor 45, diaphragms can be additionally disposed or a quantity of light of the LED 31 can be adjusted. Accordingly, based on a relative positional relationship between the index image SP and the alignment area mark AE, a judgement can be formed about an alignment state of the subject's eye E with the instrument body in up, down, right, and left directions and in addition, based on the size or density of the index image SP, a judgement can be formed about a working distance between the subject's eye E and the instrument body. At this time, if it is possible to change a magnification for observation, operational ability can be improved.

A detailed description will now be given of FIGS. 6(A), 6(B), and 6(C). FIG. 6(A) showing an ON or OFF state of the LED 31 during alignment, FIG. 6(B) showing a quantity level of received light in the ON or OFF state of the LED 31, and FIG. 6(C) showing a display state of the index image and/or the alignment area mark AE are illustrated to be correspondent to each other in the set of the figures.

The index images SP and the alignment area marks AE shown in FIG. 6(C) are those displayed on the screen 28 in a case in which alignment levels are at optional points P1 to P7, respectively.

Practically, the LED 31 blinks or is subject to modulation with higher frequency (several KHz) than that shown in FIG. 6(A) during the on-state of the LED 31 during which it looks as if the images are displayed on the screen 28 by the continuous lighting of the LED 31.

Figure 7:
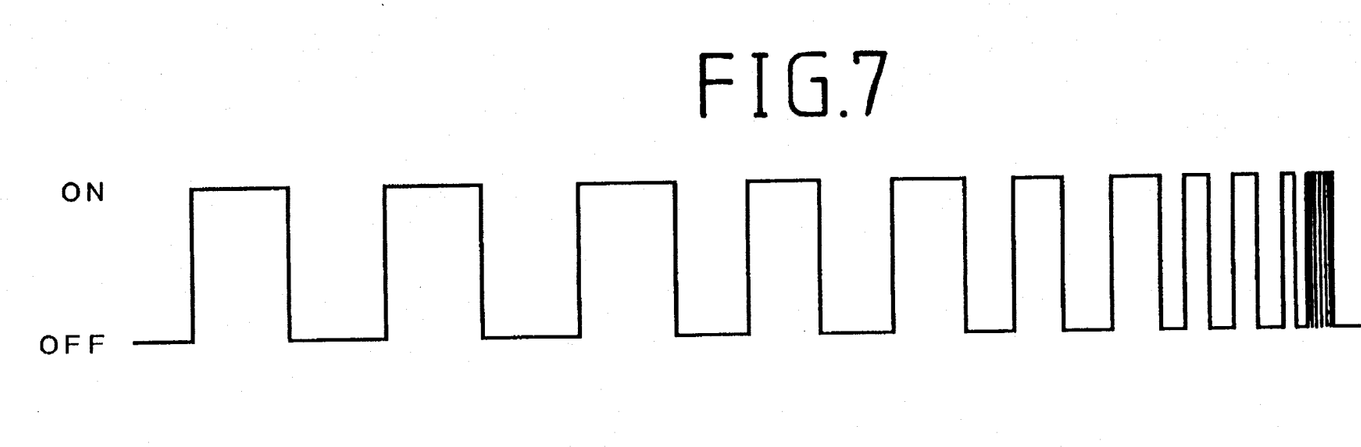
FIG. 7 is a timing chart of ON and OFF states of the alignment light source, showing an alternative of the third embodiment of the present invention.

In order to swiftly judge that the completion of alignment is nearing, blinking periods of the LED 31 can be divided smaller as shown in FIG. 7 in accordance with an alignment state.

As described in the foregoing, according to the ophthalmologic instrument of the present invention, when a desired alignment state is obtained, a display state on the displaying means is changed and thereby a working distance between the subject's eye and the instrument body can be determined while staring an index image for alignment. Accordingly, overall alignment can be easily carried out.

What is claimed is:

1. An ophthalmologic instrument comprising:
   an anterior segment illuminating light source for illuminating an anterior segment of a subject's eye;
   an alignment light projecting optical system for guiding a beam of light emitted by an alignment light source to a cornea of the subject's eye;
   an image forming optical system for forming an image of the anterior segment and an indexed image of the cornea on an image forming surface, the images being formed such that beams of light emitted by said light sources are reflected by the subject's eye;

display means for displaying the image of the anterior segment and the indexed image of the cornea formed on said image forming surface;

an alignment detecting optical system for guiding the indexed image of the cornea to light receiving means different from said image forming surface; and alignment detecting means for detecting alignment of the subject's eye with an instrument body from information about received light obtained by said light receiving means;

wherein a judgment that a desired state of alignment is nearing is formed by changing a display state of said display means in accordance with a detection result obtained by said alignment detecting means.

2. An ophthalmologic instrument as recited in claim 1, wherein a display state of said display means in a case in which the desired state of alignment is nearing is changed such that said alignment light source is changed from a lighting state to a blinking state or from a blinking state to a lighting state in accordance with a level detected by said alignment detecting means and thereby a display state of the indexed image of the cornea is changed on said display means.

3. An ophthalmologic instrument as recited in claim 1, wherein a display state of said display means in a case in which the desired state of alignment is nearing is changed such that a display state of an area mark superimposed on the indexed image of the cornea displayed on said display means is changed in accordance with a level detected by said alignment detecting means in order to indicate a reference range for guiding the indexed image of the cornea to an alignment completion position on said display means.

* * * * *